United States Patent
Baker, Jr.

(10) Patent No.: US 8,777,867 B2
(45) Date of Patent: *Jul. 15, 2014

(54) DETECTION OF OXIMETRY SENSOR SITES BASED ON WAVEFORM CHARACTERISTICS

(75) Inventor: Clark R. Baker, Jr., Castro Valley, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/526,287

(22) Filed: Jun. 18, 2012

(65) Prior Publication Data

US 2012/0259190 A1  Oct. 11, 2012

Related U.S. Application Data

(63) Continuation of application No. 11/716,437, filed on Mar. 9, 2007, now Pat. No. 8,221,326.

(51) Int. Cl.
*A61B 5/02* (2006.01)
*A61B 5/0205* (2006.01)
*A61B 5/024* (2006.01)

(52) U.S. Cl.
CPC ............. *A61B 5/024* (2013.01); *A61B 5/02416* (2013.01); *A61B 5/0205* (2013.01)
USPC .......................................... 600/500; 600/483

(58) Field of Classification Search
CPC ... A61B 5/024; A61B 5/0205; A61B 5/02416
USPC ......... 600/300–301, 323–324, 500, 501, 502, 600/503, 504, 505, 506, 507; 702/189–194
See application file for complete search history.

(56) References Cited

U.S. PATENT DOCUMENTS

| | | | |
|---|---|---|---|
| 5,058,588 A * | 10/1991 | Kaestle | ........................ 600/323 |
| 6,035,223 A | 3/2000 | Baker, Jr. | |
| 6,308,089 B1 | 10/2001 | Von Der Ruhr et al. | |
| 6,388,240 B2 | 5/2002 | Schulz et al. | |
| 6,515,273 B2 | 2/2003 | Al-Ali | |

(Continued)

FOREIGN PATENT DOCUMENTS

| JP | 27020836 A2 | 2/2007 |
|---|---|---|
| JP | 27330708 A2 | 12/2007 |

OTHER PUBLICATIONS

Shelley et al. The Detection of Peripheral Venous Pulsation Using the Pulse Oximeter as a Plethysmograph. 1993. Journal of Clinical Monitoring. 9:283-287.*

(Continued)

*Primary Examiner* — Navin Natnithithadha
*Assistant Examiner* — Eric Messersmith
(74) *Attorney, Agent, or Firm* — Fletcher Yoder PC

(57) ABSTRACT

In accordance with an embodiment of the present technique, there is provided methods and systems for detecting the location of a sensor and determining calibration algorithms and/or coefficients for calculation of physiological parameters based on the detected location. An exemplary embodiment includes receiving a signal corresponding to absorption of at least one wavelength of light by a patient's tissue, generating a plethysmographic waveform from the signal, determining an identifying characteristic of the plethysmographic waveform, and determining a location of the sensor based on a comparison of the identifying characteristic with at least one defined criterion.

20 Claims, 10 Drawing Sheets

(56) References Cited

U.S. PATENT DOCUMENTS

| | | |
|---|---|---|
| 6,560,470 B1 | 5/2003 | Pologe |
| 6,861,639 B2 | 3/2005 | Al-Ali |
| 6,979,812 B2 | 12/2005 | Al-Ali |
| 7,048,687 B1 | 5/2006 | Reuss et al. |
| 7,186,966 B2 | 3/2007 | Al-Ali |
| 7,375,347 B2 | 5/2008 | Colvin et al. |
| 7,949,380 B2 * | 5/2011 | Fein et al. .................... 600/323 |
| 2001/0045509 A1 | 11/2001 | Al-Ali |
| 2002/0038078 A1 | 3/2002 | Ito |
| 2003/0032873 A1 | 2/2003 | Diab |
| 2003/0135099 A1 | 7/2003 | Al-Ali |
| 2005/0197549 A1 * | 9/2005 | Baker, Jr. .................... 600/323 |
| 2005/0197579 A1 * | 9/2005 | Baker, Jr. .................... 600/473 |
| 2006/0206020 A1 | 9/2006 | Liao et al. |
| 2007/0043275 A1 | 2/2007 | Manheimer et al. |
| 2007/0156034 A1 | 7/2007 | Al-Ali |
| 2008/0081967 A1 | 4/2008 | Andersohn et al. |
| 2008/0081971 A1 | 4/2008 | Ollerdessen |
| 2008/0088467 A1 | 4/2008 | Al-Ali |
| 2008/0221414 A1 | 9/2008 | Baker |

OTHER PUBLICATIONS

Shelley, K.H., et al.; "Detection of Peripheral Venous Pulsation Using the Pulse Oximeter as a Plethysmograph", 1993 Journal of Clinical Monitoring 9:283-287.

* cited by examiner

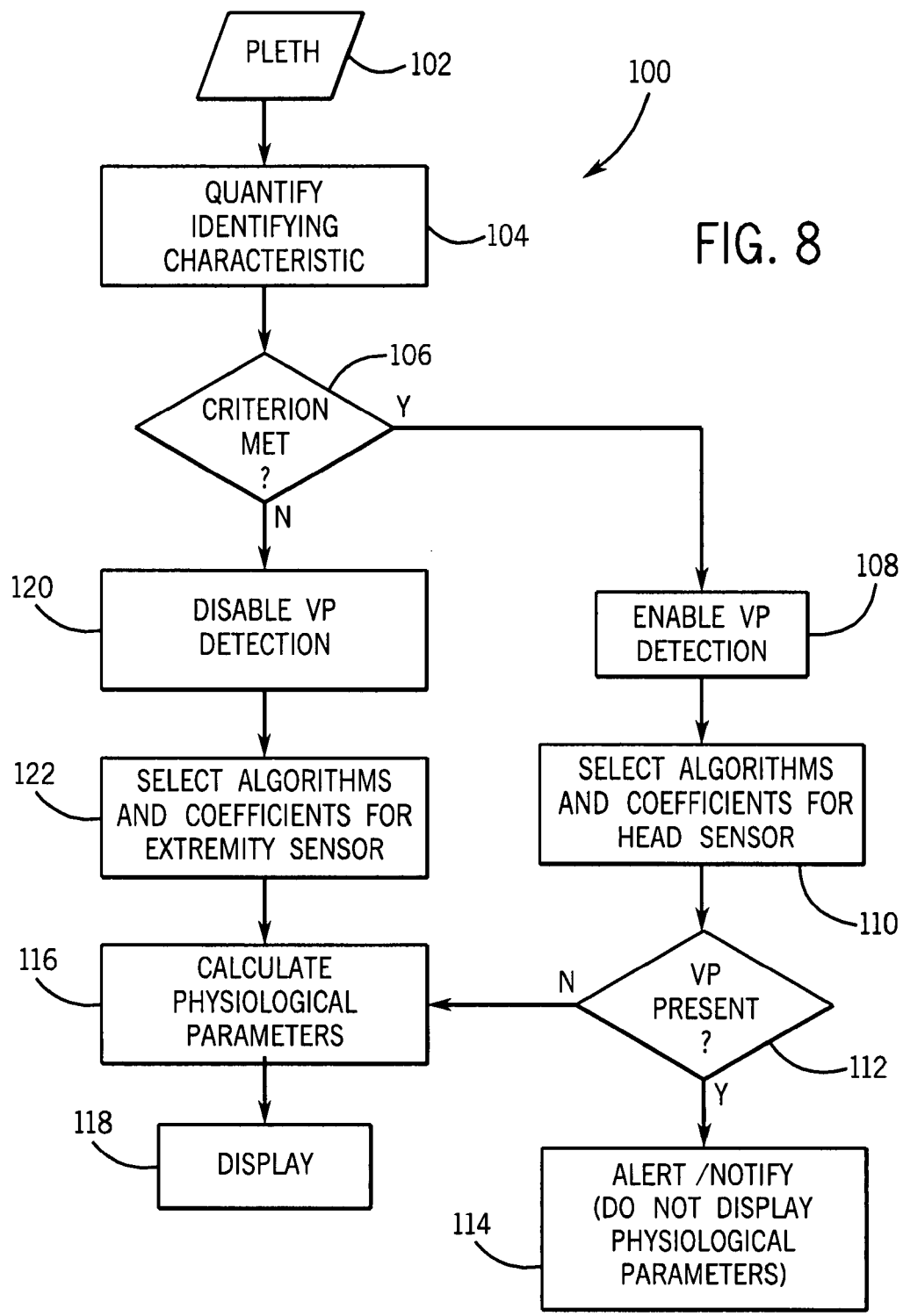

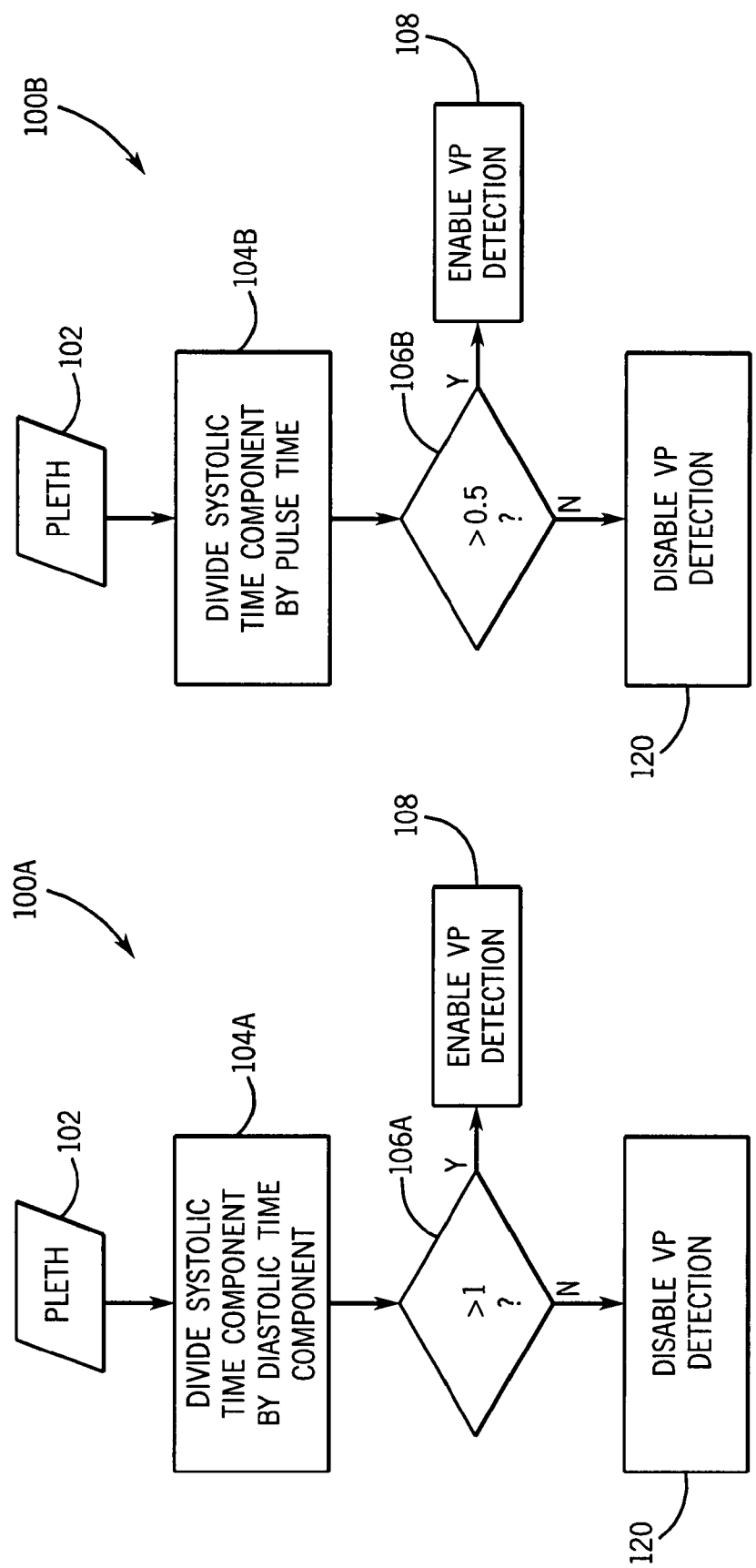

DETECTION OF OXIMETRY SENSOR SITES BASED ON WAVEFORM CHARACTERISTICS

This application is a continuation of U.S. patent application Ser. No. 11/716,437, entitled "Detection of Oximetry Sensor Sites Based on Waveform Characteristics", filed Mar. 9, 2007, which is herein incorporated by reference in its entirety.

BACKGROUND OF THE INVENTION

1. Field of the Invention

The present invention relates to pulse oximetry and, more particularly, to determining sensor location based on signal characteristics.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Sensors exist that are designed to be applied to foreheads, digits, or various other locations on a patient's body. A phenomenon called "venous pulsation" may occur in the forehead or other sites that are not on the patient's extremities. Venous pulsation refers to a pulse generated from the return flow of venous blood to the heart. Because the hemoglobin in venous blood has already delivered oxygen to tissue, sensor readings based on venous pulsation may result in artificially low calculations of blood oxygen saturation (denoted as $SpO_2$ when calculated from a pulsatile measurement). In addition, due to prominent harmonics in a venous pressure wave, pulse rate calculations based on incorrect sensor readings may be double or triple the patient's actual pulse rate. Unlike motion artifacts that may be intermittent, occurring only when a patient moves, venous pulsation can continue uninterrupted for hours. Accordingly, it may be desirable to determine when a sensor is located in an area prone to venous pulsation.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a method for detecting sensor placement, including receiving a signal corresponding to absorption of at least one wavelength of light by a patient's tissue, generating a plethysmographic waveform from the signal, determining an identifying characteristic of the plethysmographic waveform, and determining a location of the sensor based on a comparison of the identifying characteristic with at least one defined criterion.

There is further provided a system for detecting sensor placement, including a sensor having an emitter configured to emit light into a patient's tissue and a detector configured to detect the light, and a monitor having a processor configured to generate a plethysmographic waveform from the detected light, a waveform characteristic detector configured to determine an identifying characteristic of the plethysmographic waveform, and a comparator configured to determine a location of the sensor based on a comparison of the identifying characteristic with at least one criterion.

There is further provided one or more tangible, machine readable media, including code executable to perform the acts of calculating an identifying characteristic of a plethysmographic waveform and determining a location of the sensor based on a comparison of the identifying characteristic with at least one defined criterion.

There is further provided a device for detecting sensor placement, including a processor configured to generate a plethysmographic waveform from a plurality of signals corresponding to absorption of light received from a sensor emitter, a waveform characteristic detector configured to determine an identifying characteristic of the plethysmographic waveform, and a comparator configured to determine a location of the sensor based on a comparison of the identifying characteristic with at least one criterion.

BRIEF DESCRIPTION OF THE DRAWINGS

Advantages of the invention may become apparent upon reading the following detailed description and upon reference to the drawings in which:

FIG. 8 is a flow chart of a process related to determining sensor location in accordance with an exemplary embodiment of the present invention;

FIGS. 9-14 are flow charts illustrating exemplary embodiments of features of the process illustrated in FIG. 8.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Corrections may be made for venous pulsation. For example, a pulse oximetry algorithm may modify its filtering, data qualification, and/or calibration coefficients in the presence of a head or forehead sensor, since venous pulsation is more likely to occur at such sensing sites as opposed to sensing sites on a patient's extremities. Using this technique, sensors may be provided with identification information, such as the sensor name, or a bit which indicates that the sensor is designed to go on the head. This information can be read by the pulse oximeter and the appropriate algorithms may be used. These algorithms can detect venous pulsation via a phase difference between the red and IR signals and, thus, prevent the display of SpO$_2$ and pulse rate if venous pulsation is detected for a prolonged period of time, as those values may have been calculated inaccurately due to the presence of the venous pulsation. However, it is desirable that these types of site-specific algorithm modifications be used only where venous pulsation is likely to occur, and this technique may be limited when sensors are improperly placed or fail to include adequate information.

To address this concern, present embodiments are directed to a device configured to provide information about sensor placement, so that improved algorithms for calculating oxygen saturation, pulse rate, and other physiological parameters affected by venous pulsation may be utilized. Specifically, in accordance with present embodiments, a sensor emits and detects light used to calculate a patient's physiological parameters, such as, for example, pulse rate and blood oxygen saturation. The placement of the sensor is determined by analyzing characteristics of a plethysmographic waveform generated from the detected light. The detection of the sensor placement may enable an oximeter to select the appropriate algorithms and calibration information to be used for calculating the patient's physiological parameters.

Figure 1:
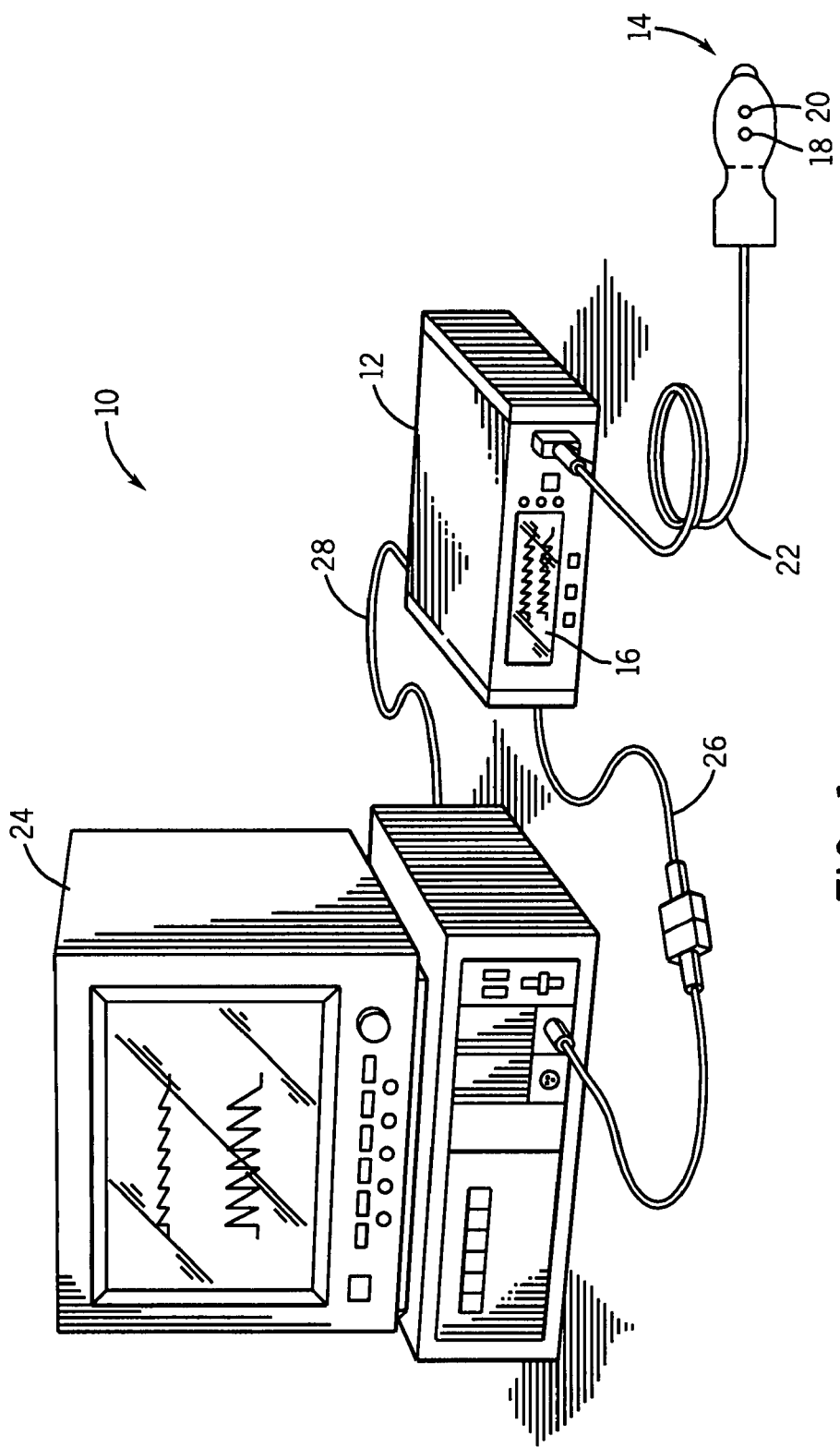
FIG. 1 is a perspective view of a pulse oximetry system coupled to a multi-parameter patient monitor and a sensor in accordance with an exemplary embodiment of the present invention.

FIG. 1 is a perspective view of a pulse oximetry system 10 in accordance with an exemplary embodiment of the present invention. The system 10 may include a pulse oximetry monitor 12 and a sensor 14. The monitor 12 may be configured to determine the placement of the sensor 14, as described below. Further, the monitor 12 may be configured to calculate physiological parameters and to display the physiological parameters and/or other information about the system on a display 16. The sensor 14 may include an emitter 18 for emitting light at certain wavelengths into a patient's tissue and a detector 20 for detecting the light after it is reflected and/or absorbed by the patient's tissue. The sensor 14 may be communicatively coupled to the monitor 12 via a cable 22 or other suitable device, such as, for example, a wireless transmission device (not shown).

The pulse oximetry system 10 may also include a multi-parameter patient monitor 24. The multi-parameter patient monitor 24 may be included in the system 10 to provide a central display for information from the monitor 12 and from other medical monitoring devices or systems (not shown). For example, the multi-parameter patient monitor 24 may display a patient's blood oxygen saturation and pulse rate information from the monitor 12 and blood pressure from a blood pressure monitor (not shown). In addition to the monitor 12, or alternatively, the multi-parameter patient monitor 24 may be configured to determine the placement of the sensor 14 and/or to calculate physiological parameters. The monitor 12 may be communicatively coupled to the multi-parameter patient monitor 24 via a cable 26 or 28 coupled to a sensor input port or a digital communications port, respectively.

Figure 2:
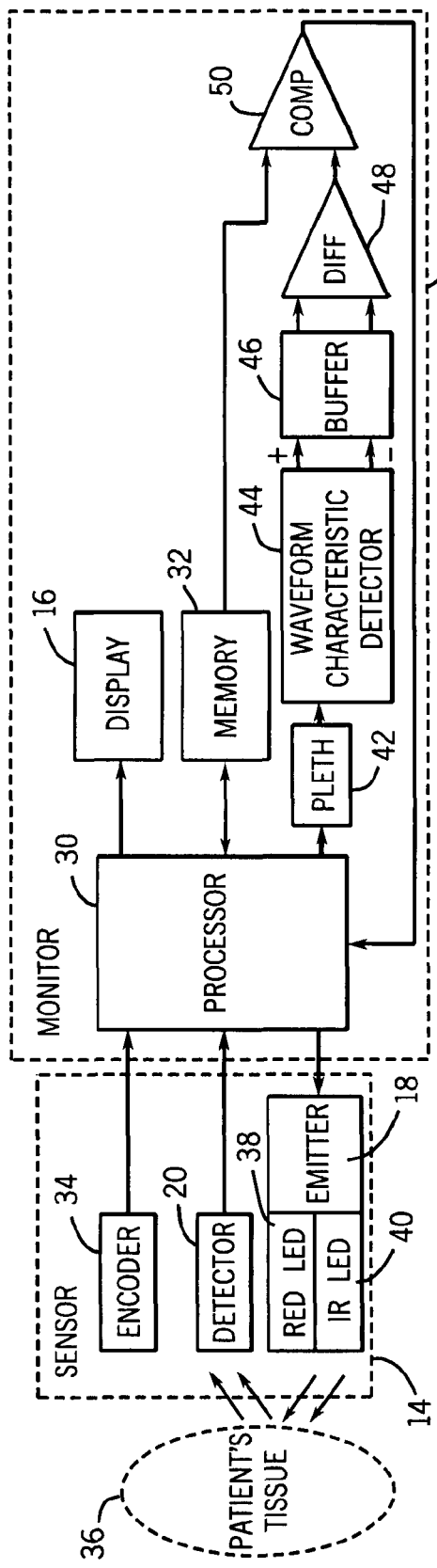
FIGS. 2-3 are block diagrams of the pulse oximetry system coupled to a patient in accordance with exemplary embodiments of the present invention.

Embodiments of the present invention may be implemented in hardware, software, or a combination thereof. Exemplary hardware is illustrated in FIG. 2, a block diagram of the exemplary pulse oximetry system 10 of FIG. 1. Specifically, certain components of the monitor 12 and the sensor 14 are illustrated in FIG. 2. The monitor 12 generally includes a processor 30, a memory 32, and the display 16. More specifically, the monitor 12 may include components found in pulse oximeters manufactured by Nellcor Puritan Bennett LLC of Pleasanton, Calif.

The sensor 14 includes the emitter 18, the detector 20, and an encoder 34. It should be noted that the emitter 18 is configured to emit at least two wavelengths of light, e.g., RED and IR, into a patient's tissue 36. Hence, the emitter 18 may include a RED LED 38 and an IR LED 40 for emitting light into the patient's tissue 36 at the wavelengths used to calculate the patient's physiological parameters. Alternative light sources may be used in other embodiments of the present invention. For example, a single wide-spectrum light source may be used, and the detector 20 may be configured to detect light only at certain wavelengths. In another example, the detector 20 may detect a wide spectrum of wavelengths of light, and the monitor 12 may process only those wavelengths which are of interest.

The detector 20 may be configured to detect the intensity of light at the RED and IR wavelengths. Light enters the detector 20 after passing through the patient's tissue 36. The detector 20 converts the intensity of the received light into an electrical signal. The light intensity is directly related to the absorbance and/or reflectance of light in the tissue 36. That is, when more light at a certain wavelength is absorbed or reflected, less light of that wavelength is received from the tissue by the detector 20. After converting the received light to an electrical signal, the detector 20 sends the signal to the monitor 12.

The encoder 34 may contain information about the wavelengths of light emitted by the emitter 18. This information may allow the monitor 12 to select appropriate calibration coefficients for calculating the patient's physiological parameters based on the wavelengths of light used. The encoder 34 may, for instance, be a coded resistor which stores values corresponding to the wavelengths of light emitted by emitter 18. These coded values may be communicated to the monitor 12, where a look-up table in the memory 32 contains calibration coefficients corresponding to the coded values. The encoder 34 may also be, for example, sensor memory on which the wavelengths of light emitted by emitter 18, the proper calibration coefficients, and/or the algorithms to be used for calculating physiological parameters may be stored for communication to the monitor 12.

The processor 30 in the monitor 12 may be configured to process incoming signals from and send control signals to the sensor 14. Intermediate hardware (not shown) may be included in the monitor 12 to filter or convert incoming signals and to implement outgoing controls. The processor 30 may then generate a plethysmographic waveform 42 based on the signals from the detector 20. The plethysmographic waveform 42 is processed in a waveform characteristic detector 44, such as, for example, a peak and/or envelope detector. Signals from the detector 44 may be stored in a buffer 46 before passing through a difference magnifier 48 where, for example, the difference between signals from the detector 44 is calculated. This difference from the difference magnifier 48 is then compared to a criterion from the memory 32, such as, for example, a threshold, in a comparator 50. In another example, the waveform characteristic detector 44 may generate a signal which is compared directly to the criterion in the comparator 50. In addition to storing criteria for determining the placement of the sensor 14, the memory 32 may contain programming to enable the processor 30 to calculate the patient's physiological parameters based on the determined placement (e.g., forehead or finger) of the sensor 14. Calculated physiological parameters may be stored in the memory 32 and/or displayed on the display 16.

Figure 3:
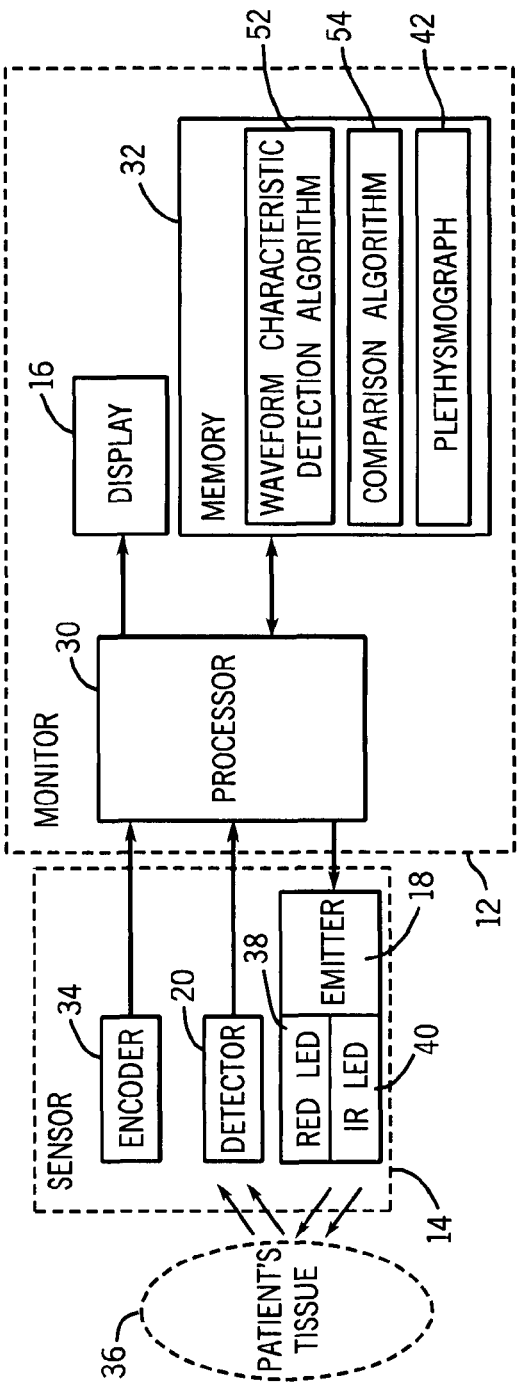

Furthermore, software may be used instead of, or in addition to, hardware to implement embodiments of the present invention. FIG. 3 illustrates exemplary software which may be utilized in the exemplary pulse oximetry system 10 of FIG. 1. Components of the monitor 12 and the sensor 14 are illustrated in FIG. 3. The monitor 12 generally includes the processor 30, the memory 32, and the display 16. More specifically, the monitor 12 may include components found in pulse oximeters manufactured by Nellcor Puritan Bennett LLC of Pleasanton, Calif. The sensor 14 includes the emitter 18, the detector 20, and the encoder 34.

The plethysmographic waveform 42 generated by the processor 30 may be analyzed by a waveform characteristic detection algorithm 52 which is stored in the memory 32. This algorithm 52 generates a waveform characteristic such as, for example, a ratio of the systolic to diastolic times or a skewness of the pulse shape, as described below. A comparison algorithm 54 then compares the waveform characteristic to the criterion stored in the memory 32 to determine whether the sensor 14 is at a location where venous pulsation is likely to occur. The processor 30 then selects calibration information and/or algorithms appropriate to the determined location.

Figure 4:
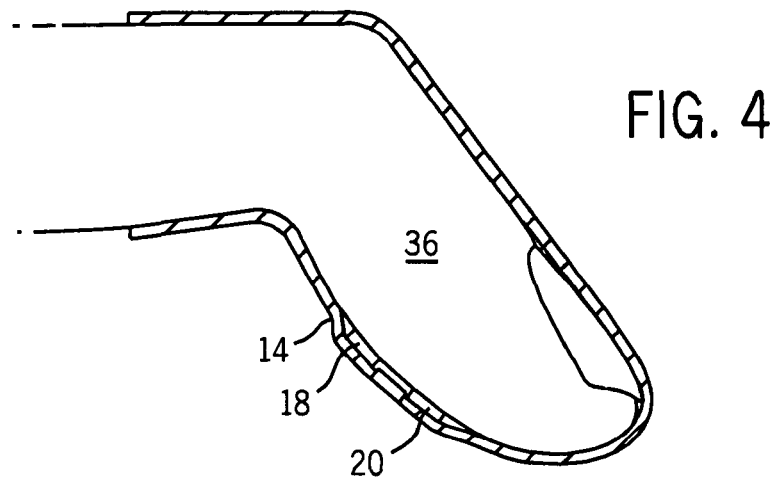
FIG. 4 illustrates the sensor applied to the patient's digit in accordance with an exemplary embodiment of the present invention.
Figure 5:
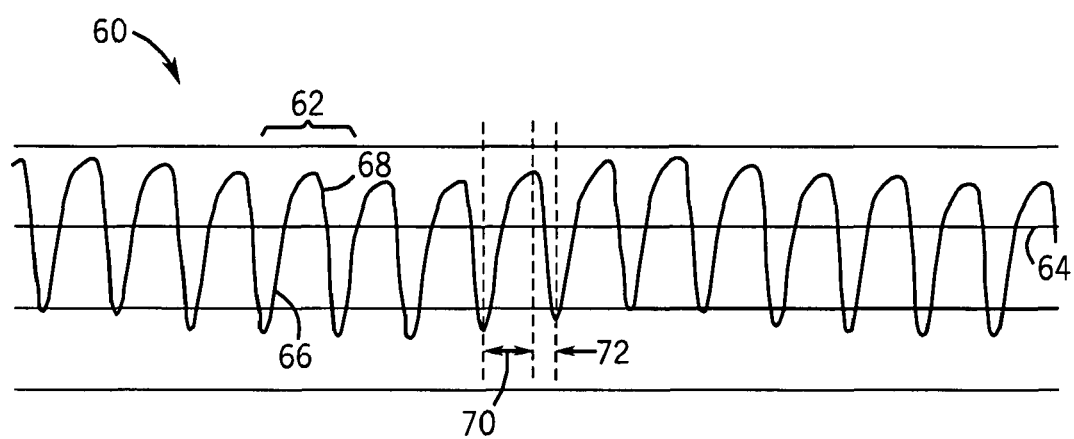
FIG. 5 is a graph illustrating the patient's observed physiological data as measured by the sensor placed on the digit in accordance with an exemplary embodiment of the present invention.

As discussed above, the sensor 14 may be placed on a patient's extremity. FIG. 4 illustrates the sensor 14 abutting the tissue 36 of a patient's finger. The emitter 18 may emit two or more wavelengths of light into the tissue 36. This light is then scattered and reflected back to the detector 20. Signals representative of the detected light are then transmitted to the monitor 12. These signals may be used to generate an optical digit plethysmograph 60, as illustrated in FIG. 5. The digit plethysmograph 60 includes high-frequency pulses 62 which generally vary around an average value, represented as a line 64. The average value line 64 may represent an average, weighted average, mean, median, or mode of pulse measurements. Each pulse 62 is representative of the patient's pulse rate and includes a diastolic component 66 and a systolic component 68. It should be noted that the systolic component of the optical digit plethysmograph 60 corresponds to the minima of the waveform, as increasing blood volume absorbs more light and reduces the light reaching the detector 20. The diastolic component 66 represents the time during which the heart is relaxed and dilating, that is, when blood is entering the heart. The systolic component 68 represents the time during which the heart is contracting, that is, when the heart is expelling blood. In the presence of only arterial pulsation, as in the digit plethysmograph 60, the diastolic component 66 has a longer time component 70 compared to a time component 72 of the systolic component 68. That is, the time 70 it takes for the signal to reach a peak is greater than the time 72 it takes for the signal to reach a valley, corresponding to maximum blood volume. A histogram of the derivative of the pulse 62 will have a negative skew because the shorter systolic component 68 creates a negative derivative of greater magnitude than a positive derivative that occurs during the diastolic component 66.

Figure 6:
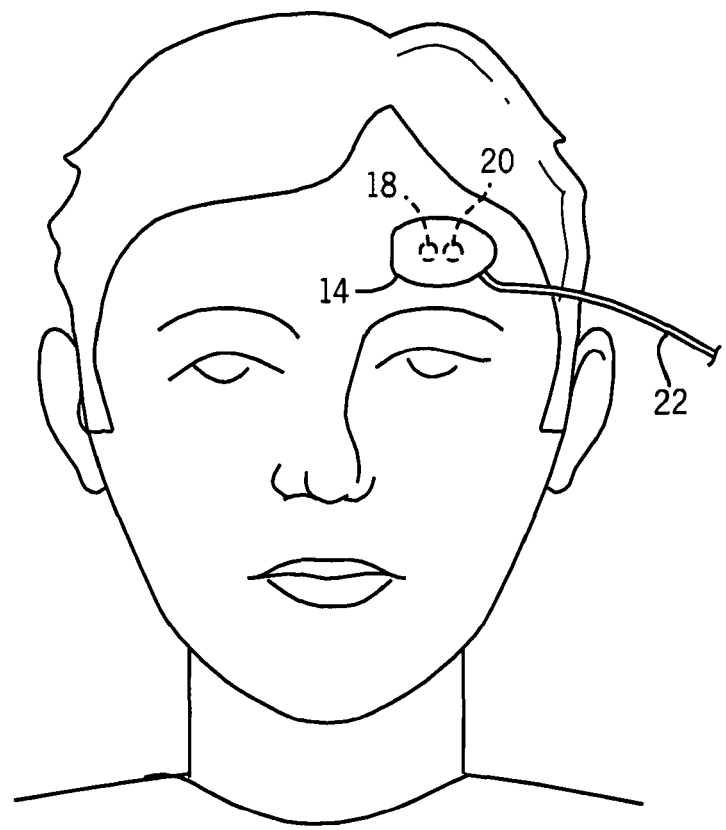
FIG. 6 illustrates the sensor applied to the patient's forehead in accordance with an exemplary embodiment of the present invention.
Figure 7:
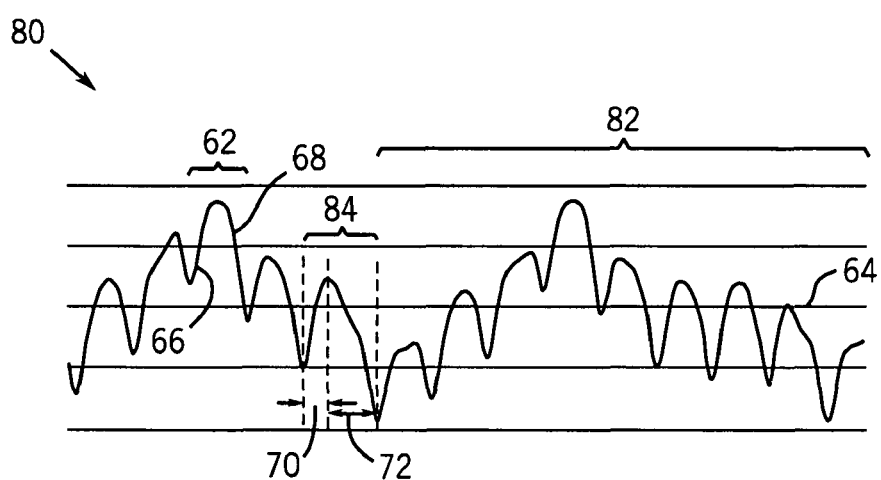
FIG. 7 is a graph illustrating the patient's observed physiological data as measured by the sensor placed on the forehead in accordance with an exemplary embodiment of the present invention.

In an alternative sensor placement, the sensor 14 is illustrated abutting the tissue 36 of a patient's forehead in FIG. 6. A forehead plethysmograph 80 generated from detected light signals is illustrated in FIG. 7. As with the digit plethysmograph 60, the pulse rate in the forehead plethysmograph 80 is represented by a high-frequency function with short pulses 62. In addition to this high-frequency function, a low-frequency function is also apparent in the forehead plethysmograph 80, illustrated as a wave 82 which varies around average value line 64. It is believed that this low-frequency function corresponds to the patient's respiratory rate. As a patient inhales, the diaphragm contracts and reduces pressure on the thoracic cavity. This reduced pressure increases the return flow of blood into the veins in the thoracic cavity from peripheral areas of the body. This venous flow particularly affects local blood volume in other areas of the body, such as the head, which are in open communication with the thoracic veins. The forehead plethysmograph 80 reflects this phenomenon as a low-frequency function at the patient's respiratory rate.

In addition, due to the presence of both arterial and venous pulsation, the diastolic component 66 and the systolic component 68 of the pulse 62 do not behave the same as they do in the presence of only arterial pulsation. That is, in some pulses 62, the diastolic time component 70 may be shorter than the systolic time component 72, as illustrated by a pulse 84. A histogram of the derivative of the pulse 84 will have a positive skew because the diastolic component 66 creates a positive derivative that is larger in magnitude than a negative derivative of the longer systolic component 68.

Furthermore, in the presence of venous pulsation, the forehead plethysmograph 80 may exhibit a preponderance of high-frequency energy due to harmonics in the venous pressure wave. That is, the pulses 62 may appear to have bumps (not shown) as a result of a high-frequency function at a harmonic of the pulse rate. Generally, this phenomenon may be most pronounced at the second and third harmonics of the pulse rate.

Present embodiments may utilize the distinctions between the digit plethysmograph 60 and the forehead plethysmograph 80 to analyze a plethysmographic waveform to determine whether the sensor 14 has been placed on a patient's forehead or digit, as described below. This determination may, among other things, allow the pulse oximetry monitor 12 to use the most effective algorithms for that sensor site in calculating a patient's physiological parameters. FIG. 8 illustrates a general process 100 for determining sensor location in accordance with an exemplary embodiment of the present invention. Examples of features of the process 100 are illustrated in FIGS. 9-12.

A waveform 102 may be generated from signals correlative of detected light, as described above with respect to the plethysmographs 60 and 80, for example. An identifying characteristic of the waveform 102 is then quantified (Block 104). The waveform characteristic may include, for example, the shape of the pulse 62, a preponderance of low-frequency energy about the patient's respiratory rate, or a preponderance of high-frequency energy about a harmonic of the patient's pulse rate, as described below. The waveform characteristic is then analyzed against at least one criterion, as described below, to determine whether the sensor 14 is located at a site where venous pulsation is likely to occur (Block 106).

If the criterion is met, this indicates that the sensor is placed at a site where venous pulsation is likely to occur, thus detection of venous pulsation is enabled (Block 108). Enabling detection of venous pulsation entails selecting algorithms and/or calibration information designed for use with a forehead sensor (Block 110). Exemplary algorithms for detecting and/or reporting venous pulsation are described in U.S. patent application Ser. No. 10/796,584, filed Mar. 8, 2004, entitled "METHOD AND APPARATUS FOR OPTICAL DETECTION OF MIXED VENOUS AND ARTERIAL BLOOD PULSATION IN TISSUE" by Clark R. Baker, Jr., U.S. patent application Ser. No. 11/528,295, filed Sep. 27, 2006, entitled "METHOD AND APPARATUS FOR DETECTION OF VENOUS PULSATION" by Clark R. Baker, Jr., U.S. patent application Ser. No. 11/716,132, filed concurrently herewith, entitled "SYSTEM AND METHOD FOR VENOUS PULSATION DETECTION USING NEAR INFRARED WAVELENGTHS" by Clark R. Baker, Jr., and U.S. patent application Ser. No. 11/716,263, filed concurrently herewith, entitled "SYSTEM AND METHOD FOR DETECTION OF VENOUS PULSATION" by Clark R. Baker, Jr. and Paul Mannheimer, all of which are herein incorporated by reference in their entirety for all purposes. Based on the proper algorithms and/or calibration coefficients, a determination is made as to whether or not venous pulsation is present (Block 112). If venous pulsation is present, a caregiver is alerted via, for example, an audible alarm, a visible display, or the lack of display of physiological parameters (Block 114). If venous pulsation is not detected, the selected algorithms and/or calibration coefficients are used to calculate physiological parameters (Block 116). The calculated physiological parameters may then be displayed (Block 118), for example, on the display 16.

If, upon analysis (Block 106), the waveform characteristic does not meet the criterion, detection of venous pulsation is disabled (Block 120). Algorithms and/or calibration information designed for use with extremity sensors are selected (Block 122), and physiological parameters are calculated based on this selected information (Block 116). The calculated physiological parameters may then be displayed (Block 118).

Example embodiments of features of the process 100 are illustrated in FIGS. 9-14. Specifically, these embodiments illustrate examples of the waveform characteristic which may be quantified and analyzed to determine placement of the sensor 14. As such, the steps of process 100 after which venous pulsation detection is either enabled (Block 108) or disabled (Block 120) are not shown. It should be appreciated by one skilled in the art that the quantification and analysis steps described may be performed by hardware or software, as illustrated in FIGS. 2-3. FIGS. 9-12 illustrate embodiments of the process 100 in which the identifying characteristic of the waveform 102 quantified in Block 104 is the shape of the pulses 62.

Specifically, as illustrated by a process 100A in FIG. 9, a ratio of the systolic time component 72 to the diastolic time component 70 may be calculated. The systolic time component 72 is divided by the diastolic time component 70 (Block 104A). The resulting ratio is then analyzed against a criterion (Block 106A). In this embodiment, if the ratio is greater than one, this indicates that the diastolic time component 70 is shorter than the systolic time component 72, as illustrated by the pulse 84 in FIG. 7. As described above, this phenomenon is indicative of placement of the sensor 14 on the forehead or an area not on an extremity. Therefore, if the ratio is greater than one, detection of venous pulsation is enabled (Block 108), and if the ratio is less than one, detection of venous pulsation is disabled (Block 120). One skilled in the art will recognize that this threshold may be refined based on empirical data.

An alternative ratio, illustrated in a process 100B in FIG. 10, compares the systolic time component 72 to the time of the entire pulse 62. This ratio may be calculated (Block 104B) and analyzed against the criterion (Block 106B). If the systolic time component 72 is greater than half of the entire pulse time, as illustrated by the pulse 84 in FIG. 7, the sensor 14 may be located at a site where venous pulsation is likely to occur. As such, venous pulsation detection is enabled (Block 108). If the ratio of the systolic time component 72 to the entire pulse time is less than half, as illustrated by the pulses 62 in FIG. 5, venous pulsation detection is disabled (Block 120). It should be understood by one skilled in the art that the ratio of any two of the systolic time component 72, the diastolic time component 70, and the pulse time may be utilized to characterize the pulse shape as described here. A corresponding threshold may then be used as the analysis criterion in Block 106.

Figure 11:
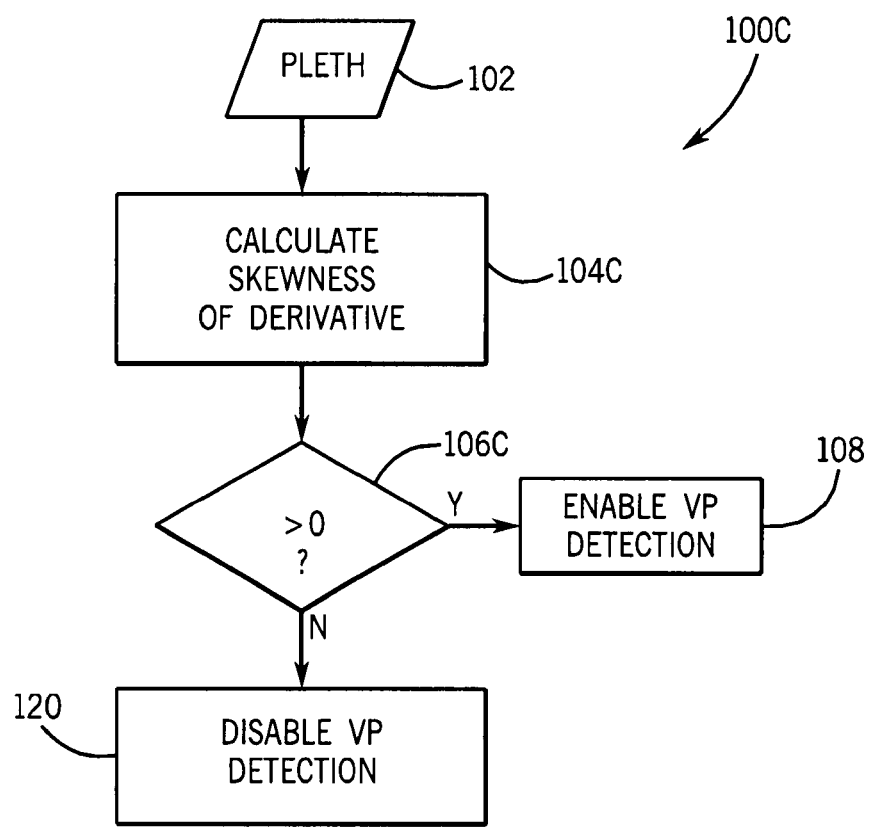

An alternative measure of the shape of the pulses 62 is the skewness of the derivative of the plethysmograph, as illustrated in a process 100C in FIG. 11. Skewness is a measure of the asymmetry of a distribution about its mean. Skewness may be calculated according to the following equations:

$$Skew_t = \frac{n \sum (x_t - \bar{x})^3}{(n-1)(n-2)\sigma^3}, \quad (1)$$

where x refers to a plurality of samples of the derivative of the IR or Red plethysmographic signal corresponding to at least one pulse period 62 in the waveform 102, n is the number of samples in the plurality of samples, σ is the standard deviation of x, and t indicates the number of the sample. Skewness is calculated (Block 104C) and analyzed (Block 106C). If the skewness is positive (i.e., greater than zero), as illustrated by the pulse 84 in FIG. 7, this indicates that the sensor 14 is located at a site where venous pulsation is likely to occur, therefore detection of venous pulsation is enabled (Block 108). If the skewness is negative, or less than zero, detection of venous pulsation is disabled (Block 110). In addition, a more precise skewness threshold may be determined. That is, a threshold may be determined empirically which accounts for the expected skewness for a given patient or system. For example, the derivative of a digit plethysmograph 60 for a given patient may have a skewness of −1.2, while the derivative of a forehead plethysmograph 80 from the typical patient may have a skewness of −0.4, therefore the analysis threshold may be −0.8 rather than zero.

Figure 12:
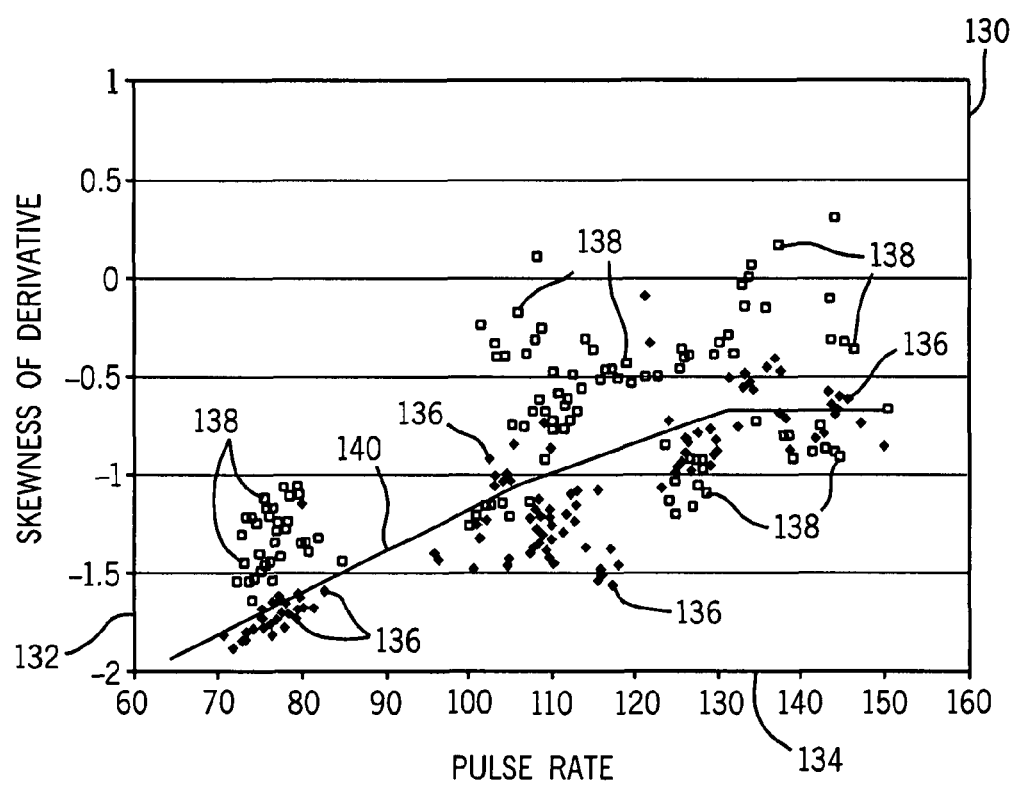

Additionally, the skewness of the derivative of the plethysmograph may be more predictive of sensor location when combined with the patient's observed pulse rate. FIG. 12 illustrates in a graph 130 the relationship between the skewness of the derivative of the plethysmograph on a y-axis 132 and the pulse rate on an x-axis 134. Data points 136 were collected from a sensor 14 placed on a patient's digit, and data points 138 are from a sensor 14 placed on a patient's forehead. The patient's pulse rate may be used to determine the analysis criterion such that, for example, where a patient has a pulse rate of 130 the analysis threshold may be −0.5 rather than −0.8. An exemplary analysis criteria curve is illustrated by a line 140.

Figures 13, 14:
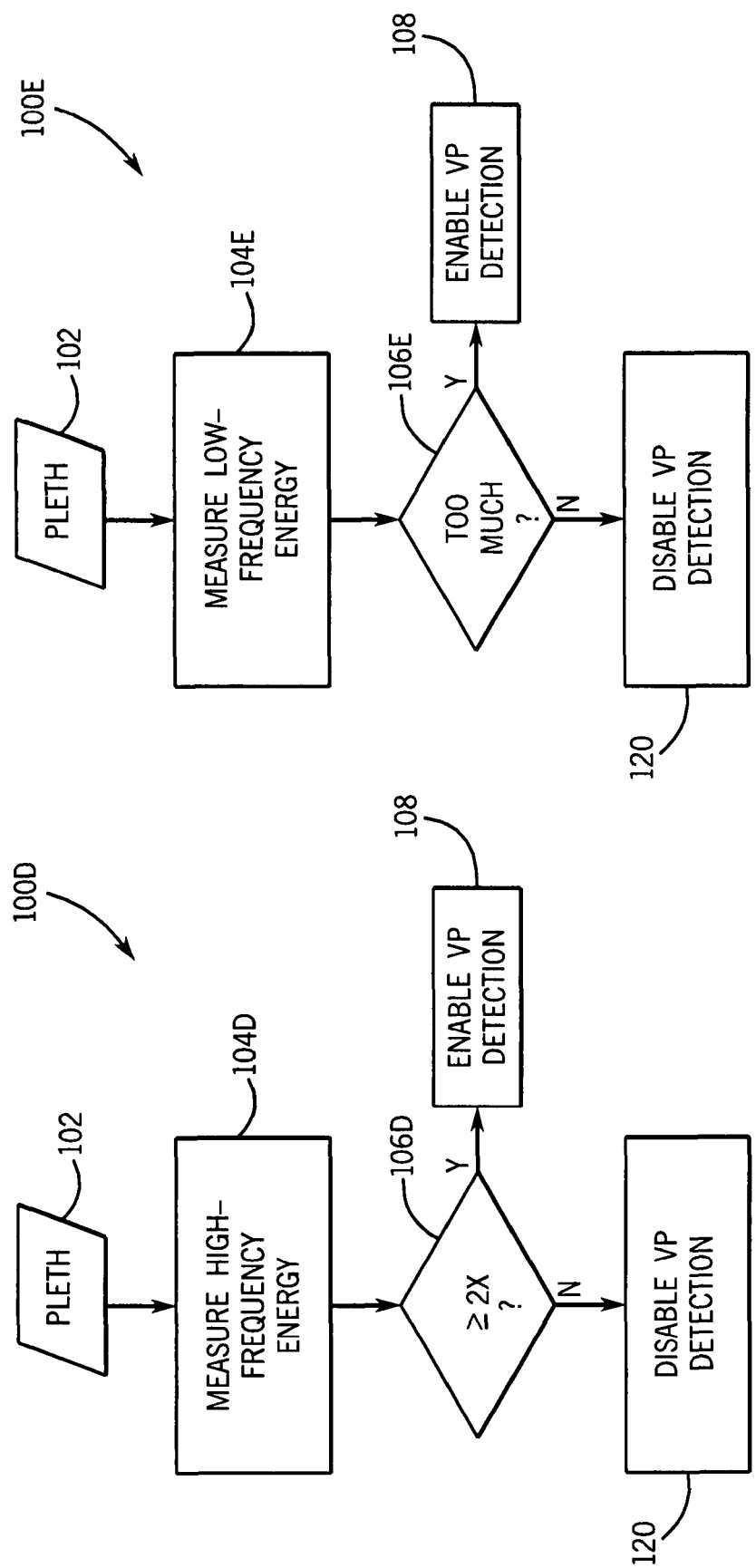
Figure 15:
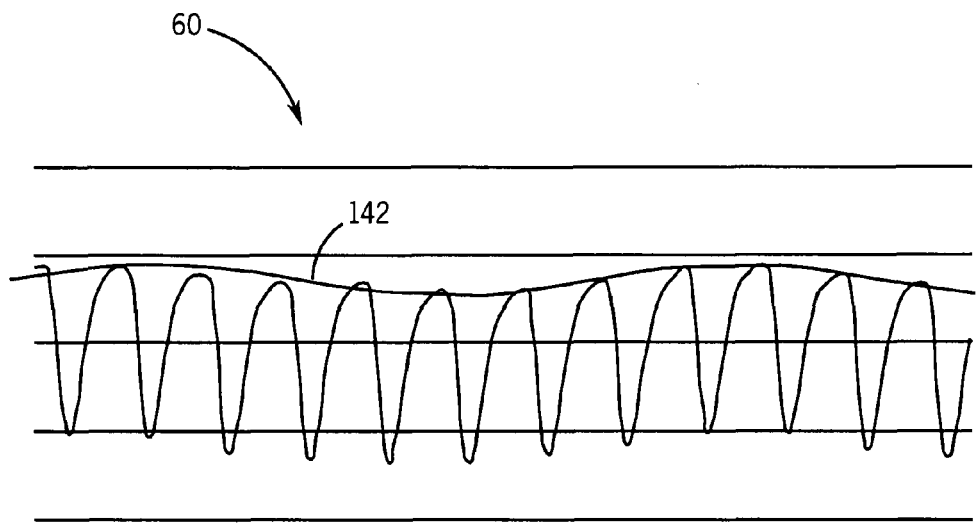
FIGS. 15-16 are graphs illustrating a low-frequency function in the graphs of FIGS. 5 and 7 in accordance with an exemplary embodiment of the present invention.
Figure 16:
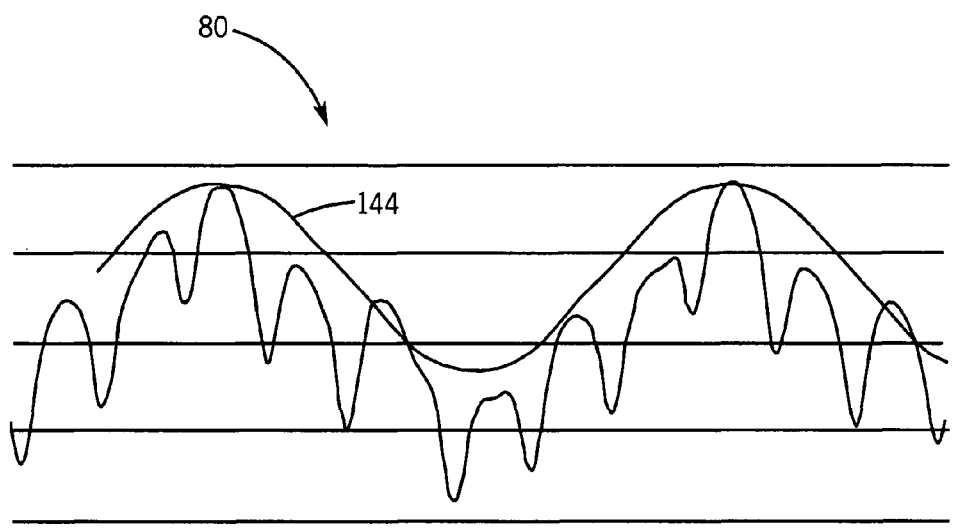

In addition to analyzing the shape of the pulses 62, as described above, the process 100 may be designed to detect a preponderance of high- and/or low-frequency energy in the waveform 102, as illustrated in FIGS. 13-16. FIG. 13 illustrates a process 100D where high-frequency energy characterizes the waveform 102. A preponderance of high-frequency energy may be indicative of the presence of venous pulsation. That is, when the pulses 62 exhibit bumps, or squiggles, at or near harmonics of the pulse rate, this is generally due to venous pulsation. As such, where these bumps are present in the waveform 102, the sensor 14 is located at a site where venous pulsation may occur. The high-frequency energy is measured (Block 104D) and analyzed against a criterion (Block 106D). Detection and analysis of this high-frequency function may be accomplished by, for example, taking a derivative of the waveform 102 and comparing the frequency at which the derivative function crosses zero to the expected frequency, given a patient's pulse rate. If, for example, the actual frequency is at least about two times the expected frequency, there is a preponderance of high-frequency energy in the waveform 102. As such, venous pulsation detection is enabled (Block 108). If the actual frequency is approximately equivalent to the expected frequency, venous pulsation detection is disabled (Block 120).

FIG. 14 illustrates a process 100E where low-frequency energy characterizes the waveform 102. The shape of a low-frequency function from the digit plethysmograph 60 is illustrated as a wave 142 in FIG. 15. Likewise, the shape of a low-frequency function from the forehead plethysmograph 80 is illustrated as a wave 144 in FIG. 16. The waves 142 and 144 may be generated, for example, by an envelope detector. The strength, or amplitude, of the low-frequency waves 142 and 144 may be measured (Block 104E) relative to the strength of the higher-frequency waves corresponding to the patient's cardiac pulse. The analysis criterion against which the low-frequency energy is compared (Block 106E) may be determined empirically for a given monitor 12 or system 10 due to variations in the amplitude of waveforms 102 generated by different systems. That is, the wave 142 from the digit plethysmograph 60 of one monitor 12 may have a similar amplitude to the wave 144 from the forehead plethysmograph 80 of another monitor 12. If the strength of the low-frequency wave 142 or 144 exceeds the threshold for a given system, detection of venous pulsation is enabled (Block 108). If the threshold is not exceeded, venous pulsation detection is disabled (Block 120).

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized in conjunction with the measurement and/or analysis of carboxyhemoglobin, methemoglobin, total hemoglobin, intravascular dyes, and/or water content. Likewise, the technique may be employed using other techniques for measuring pulse shape, different sequences of filtering, different constants, and so forth. The invention is to cover all modifications, equivalents, and alternatives falling within the spirit and scope of the invention as defined by the following appended claims.

What is claimed is:

1. A method for detecting sensor placement, comprising:
   receiving a signal corresponding to absorption of at least one wavelength of light by a patient's tissue;
   generating a plethysmographic waveform from the signal;
   determining an identifying characteristic of the plethysmographic waveform using a processor; and
   determining a physical location of the sensor on the patient's body based on a comparison of the identifying characteristic with defined criteria associated with different physical locations on the patient's body using the processor, wherein determining the physical location of the sensor comprises determining whether the physical location of the sensor is a location on an extremity of the patient's body or a location other than an extremity of the patient's body.

2. The method of claim 1, comprising determining calibration algorithms, calibration coefficients, or a combination thereof based on the physical location of the sensor.

3. The method of claim 2, comprising calculating a physiological parameter based on the calibration algorithms, calibration coefficients, or combination thereof.

4. The method of claim 1, wherein the identifying characteristic of the plethysmographic waveform comprises a shape of a pulse in the plethysmographic waveform.

5. The method of claim 4, wherein determining the physical location of the sensor comprises calculating a ratio of at least two of a systolic time component of the pulse, a diastolic time component of the pulse, and a total pulse time.

6. The method of claim 4, wherein the pulse shape comprises a skewness of a derivative of the pulse.

7. The method of claim 1, wherein at least one criterion of the defined criteria is determined by a patient's pulse rate.

8. The method of claim 1, wherein the identifying characteristic of the plethysmographic waveform comprises a strength of a low frequency portion of the plethysmographic waveform at about a respiratory rate of the patient.

9. The method of claim 1, wherein the identifying characteristic of the plethysmographic waveform comprises a strength of a high-frequency portion of the plethysmographic waveform at about a harmonic of a pulse rate of the patient.

10. The method of claim 1, wherein at least one criterion of the defined criteria comprises a threshold value.

11. The method of claim 1, comprising enabling detection of venous pulsation based on the physical location of the sensor.

12. A system for detecting sensor placement, comprising:
   a sensor having a detector configured to detect the light; and
   a monitor configured to
      generate a plethysmographic waveform from the detected light, determine an identifying characteristic of the plethysmographic waveform, and determine a physical location of the sensor on a patient's body based on a comparison of the identifying characteristic with defined criteria associated with different physical locations on the patient's body, wherein the physical location of the sensor on a patient's body is selected from the group consisting of a location on an extremity of the patient's body and a location other than an extremity of the patient's body.

13. The system of claim 12, wherein the monitor is configured to determine calibration algorithms, calibration coefficients, or a combination thereof based on the physical location of the sensor.

14. The system of claim 13, wherein the monitor is configured to calculate a physiological parameter based on the calibration algorithms, the calibration coefficients, or the combination thereof.

15. The system of claim 12, wherein the identifying characteristic of the plethysmographic waveform comprises a shape of a pulse in the plethysmographic waveform.

16. The system of claim 12, wherein the monitor comprises a comparator configured to determine the physical location of the sensor based on a comparison of the identifying characteristic with the criteria associated with the different physical locations on the patient's body, wherein the comparator comprises a hardware comparator, a comparison algorithm stored on a non-transitory computer readable medium, or a combination thereof.

17. A device for detecting sensor placement, comprising:
a processor configured to
generate a plethysmographic waveform from a plurality of signals corresponding to absorption of light received from a sensor, determine an identifying characteristic of the plethysmographic waveform, and determine a physical location of the sensor on a patient's body based on a comparison of the identifying characteristic with defined criteria associated with different physical locations on the patient's body, wherein the physical location of the sensor on a patient's body is selected from the group consisting of a location on an extremity of the patient's body and a location other than an extremity of the patient's body.

18. The device of claim 17, wherein the processor is configured to determine calibration algorithms, calibration coefficients, or a combination thereof based on the physical location of the sensor.

19. The device of claim 18, wherein the processor is configured to calculate a physiological parameter based on the calibration algorithms, the calibration coefficients, or the combination thereof.

20. The device of claim 17, wherein the processor is configured to enable venous pulsation detection based on the physical location of the sensor.

* * * * *